United States Patent [19]
Ishioka et al.

[11] 3,957,804
[45] May 18, 1976

[54] METHOD FOR THE PRODUCTION OF NICOTINAMIDE AND ISONICOTINAMIDE

[75] Inventors: Ryoji Ishioka, Tokyo; Norio Kametaka, Hiratsuka; Kuniomi Marumo, Fujisawa, all of Japan

[73] Assignee: Showa Denko Kabushiki Kaisha, Tokyo, Japan

[22] Filed: Sept. 4, 1975

[21] Appl. No.: 610,406

[30] Foreign Application Priority Data

Sept. 11, 1974 Japan.............................. 49-103789

[52] U.S. Cl................... 260/295 AM; 260/295.5 A; 252/472
[51] Int. Cl.²....................................... C07D 213/56
[58] Field of Search ............. 260/295.5 A, 295 AM

[56] References Cited
OTHER PUBLICATIONS

Sakai et al., Chem. Abstracts, Vol. 68 (3), 12,249(e), Jan. 1968.

Inoue et al., Chem. Abstracts, Vol. 72 (25), 132,554e, June 1970.

Yukio et al., Chem. Abstracts, Vol. 81, (17), 105297c, Oct. 1974.

*Primary Examiner*—Alan L. Rotman
*Attorney, Agent, or Firm*—Fitzpatrick, Cella, Harper & Scinto

[57] ABSTRACT

A method for the production of nicotinamide or isonicotinamide by catalytically hydrating 3- or 4-cyanopyridine which is characterized in that the hydration reaction is carried out in the presence of a nickel oxide/iron oxide combined catalyst.

9 Claims, No Drawings

METHOD FOR THE PRODUCTION OF NICOTINAMIDE AND ISONICOTINAMIDE

This invention relates to a method for the production of nicotinamide or isonicotinamide by catalytically hydrating 3- or 4-cyanopyridine, respectively, which is characterized in that the hydration reaction is carried out in the presence of a nickel oxide/iron oxide combined catalyst. The nicotinamide and isonicotinamide will be hereinafter referred to simply as the pyridine carboxylic acid amide, and 3- and 4-cyanopyridine, as the cyanopyridine.

It is known that the pyridine carboxylic acid amide can be obtained through catalytic hydration of the cyanopyridine. As the catalyst useful for that purpose, for example, conc. sulfuric acid, alkaline hydrogen peroxide, and a minor amount of an alkaline substance such as caustic soda or sodium carbonate, have been proposed. However, when such known catalysts are used, substantial amounts of pyridine carboxylic acid is by-produced concurrently with the intended pyridine carboxylic acid amide, to reduce the total yield of the acid amide. Although the catalyst composed of the minor amount of the alkaline substance gives relatively high theoretical yield of the acid amide, it fails to give a satisfactorily high conversion of the cyanopyridine. Furthermore, the separation and refining of the object acid amide from the reaction mixture which also contains the unreacted cyanopyridine, by-produced alkali carboxylate, and the alkaline solution of the catalyst requires extremely complicated and cumbersome procedures.

We have engaged in extensive studies on the possibility of using a solid catalyst which is insoluble in the reaction liquid, to find that the combined oxide catalyst consisting essentially of nickel oxide and iron oxide is highly effective for the intended hydration reaction, overcomeing the various disadvantages incidental to the known soluble catalysts.

The use of nickel oxide as the catalyst for the hydrating reaction of 3-cyanopyridine was disclosed in Bull. Chem. Soc. Japan, Vol. 40, p. 1660 (1967). However, the catalytic activity reported in the prior art is low, the reaction requires normally such long time as seven to ten hour, and furthermore the yield of the nicotinamide is low. Whereas, so far as we are aware, there is no prior art reporting on the use of iron oxide as a hydration catalyst of cyanopyridine. In fact, an iron oxide used as the hydration catalyst gives only a very low conversion.

It is indeed surprising, therefore, that the use of the nickel oxide/iron oxide combined catalyst according to the invention achieves the high conversion and selectivity which could never be attained by using either the nickel oxide or iron oxide catalyst alone, by the synergistic effect of the two components. Furthermore, the combined catalyst exhibits very long life. Thus the combined catalyst is characterized by its high catalytic activity and conversion to the object product, long catalyst life, and easy separation from the reaction mixture.

Hereinafter the invention will be described in further details as to the preferred embodiments thereof.

The atomic ratio of Ni to Fe in the nickel oxide/iron oxide combined catalyst is variable over a broad range. Normally it is appropriate to select the atomic ratio within the range of 100:1 to 1:100, particularly of 10:1 to 1:10 with favorable results. Generally speaking, the higher the ratio of Ni, the higher the selectivity, but excessively high Ni content gives rise to the decreasing tendency of the conversion.

The preparation of the catalyst may follow the established practices for making solid oxide catalysts in general. That is, the catalyst can be prepared by calcining an intimate mixture of nickel hydroxide and iron hydroxide to convert them to the corresponding oxides. Such intimate mixtures of the hydroxides can be formed, in a simplest embodiment, by the means normally referred to as co-precipitation. Such co-precipitation method comprises adding to a mixed aqueous solution containing as dissolved therein water-soluble inorganic or organic salts of nickel and iron, for example, halides, nitrates, sulfates, formates, acetates, propionates, oxalate, succinates, etc., at a prescribed quantitative ratio, a water-soluble basic substance, preferably an alkali metal hydroxide, carbonate or bicarbonate, such as NaOH KOH, $Na_2CO_3$, $NaHCO_3$ and ammonium carbonate or bicarbonate, to cause the simultaneous precipitation of the hydroxides of nickel and iron; filtering the resulting intimate mixture of the hydroxides; washing the remaining solid with water; and drying the product. On the other hand, such an intimate mixture of the hydroxides may be prepared by other methods, such as kneading the nickel hydroxide and iron hydroxide which have been separately prepared in advance, together thoroughly with water, or thoroughly mixing the powdery components by a mechanical means, such as a grinder. In still another embodiment, an intimate mixture of water-soluble salts of nickel and iron can be calcined and converted to that of the oxides to serve as the catalyst. The intimate mixture of the water-soluble salts can be obtained by, for example, pulverizing and mixing together a nickel salt and iron salt as already named, or by concentrating and drying a mixed aqueous solution of those salts. Furthermore, the combined catalyst may be formed by mixing nickel oxide and iron oxide which have been separately prepared in advance, at a predetermined quantitative ratio, and mechanically grinding the mixture; or by mixing the separately pulverized nickel oxide and iron oxide at a predetermined quantitative ratio.

While the catalyst to be used in this invention can be prepared by any of the above-described methods, the combined catalyst obtained by calcining an intimate mixture of the hydroxides obtained by the co-precipitation method, or an intimate mixture of the water-soluble salts, particularly the former, is preferred. Of the preferred catalysts, the most preferred is the combined catalyst obtained by calcining an intimate mixture of hydroxides of nickel and iron precipitated concurrently by adding to nitrates or sulfates of nickel and iron, ammonium carbonate, sodium carbonate, or sodium hydroxide. The calcined product can be easily shaped into the desired form which seldom crumbles during usage. The combined oxide catalyst may be, if desired, used as supported on a suitable carrier, such as activated alumina, diatomaceous earth, active carbon, silica gel, molecular sieve, etc. However, the combined nickel oxide/iron oxide itself is easily moldable, seldom crumbles and exhibits fully satisfactory catalytic activity, and therefore is quite sufficient for practical use without the carrier.

The calcination of the intimate mixture of the hydroxides or of the water-soluble salts is performed normally at the temperatures ranging from 100° to 1000°C., preferably 200° – 800°C., particularly 300° – 600°C. The mixture is treated at a temperature within the specified range for approximately 2 to 10 hours while air is passed through the system.

The microscopic structure and mechanism of activity of the subject catalyst are not fully clear, but it can be surmised from the optimum range of atomic ratio between nickel and iron and the influence of the method of catalyst preparation, on the catalytic performance, that as a possibility the nickel oxide and iron oxide in the catalyst are not entirely present simply as a physical mixture, but nickel, iron, and oxygen may be chemically combined to form so to speak a composite oxide which presumably contributes considerably to the catalytic performance. In fact, however, it seems most appropriate to think that the nickel oxide, iron oxide, and nickel-iron composite oxide are concurrently present at suitable quantitative ratios, to mutually act on the others to exhibit the excellent catalytic ability.

The hydration reaction of the cyanopyridine in the presence of the combined oxide catalyst can be effected at the temperatures ranging from room temperature to 300°C. The higher the reaction temperature, the greater the rate of reaction, but the occurrence of side reaction also tends to increase to lower the selectivity for the object acid amide. Therefore, the practically preferred reaction temperature ranges from 50° to 200°C.

Obviously, the hydration reaction is performed in the concurrent presence of water. While the reaction can proceed in the presence of the water no greater than the equivalent to the starting cyanopyridine, normally 1 – 100 times the stoichiometric amount of water is used. Preferably 5 to 50 times the stoichiometric amount of water is used, which is desirable also from the standpoints of reaction rate and separation and recovery procedures of the object product.

The reaction can be effected at vapor phase, but normally liquid phase is selected with convenience. Either a batch system or continuous operation system can be employed, and the catalyst may be used in any form such as a fixed bed, suspended bed, or other conventionally practiced catalytic system.

The reaction time is variable depending on the reaction temperature selected, amounts of the catalyst and water, etc. Generally speaking, however, if the reaction is performed batchwise, 2 to 4 hours' reaction under suitable conditions gives the satisfactory result.

There is no critical limit to the amount of the catalyst. The greater the amount of the catalyst, the greater the reaction rate, and the shorter the reaction time. From the practical standpoint, however, it is appropriate to use approximately 25 – 200% by weight to the equivalent of starting cyanopyridine, if the reaction is performed batchwise. The catalyst used in the batch system can be separated from the liquid reaction mixture, and repeatedly used in the reaction as it is.

When the subject method is practiced by a continuous flow system, the catalyst is preferably given granular or pelletized form to insure the sufficient contact with the aqueous cyanopyridine solution. The grain size is optional within the limit to allow smooth flow of the aqueous solution, but normally that of 0.1 mm – 6 mm in average diameter is preferred to obtain a suitable reaction rate. It is relatively easy to feed liquid cyanopyridine to the reactor, because it has a low melting point, but normally it is conveniently supplied to the reactor as an aqueous solution. The flow rate of the aqueous cyanopyridine solution is variable, depending on such factors as the grain size of catalyst, reaction temperature, concentration of the solution, etc., but normally the suitable contact time ranges from 10 minutes to 5 hours. In order for obtaining a sufficiently high conversion, 20 minutes to 3 hours' reaction is appropriate.

Example 1

291 Grams of nickel nitrate [$Ni(NO_3)_2 \cdot 6H_2O$] and 81 g of ferric nitrate [$Fe(NO_3)_3 \cdot 9H_2O$] were dissolved in 1.2 liters of water. Separately, 219 g of ammonium carbonate was dissolved in one liter of water, and the two solutions were simultaneously dropped into 300 cc of water, while maintaining the pH of the system at 8.3. Thus formed precipitate was recovered by filtration washed with water, dried in vacuum drying apparatus at 110°C. for 9 hours, and then calcined in air, at 400°C. for 3 hours, to form a combined oxide catalyst of the invention.

Into a 20-ml glass ampoule, 1 g of the above catalyst and 10 cc of a 10% (weight/volume) aqueous solution of 3-cyanopyridine were sealed, and the ampoule was placed in a thermostat with shaking apparatus. The hydrating reaction was effected at 135°C. for 2 hours. After completion of the reaction, the ampoule was quenched and unsealed. The catalyst was recovered by filtration, and washed with water. The washing was combined with the filtrate, and its contents of unreacted 3-cyanopyridine and nicotinamide formed were determined by gas-chromatography. Also a part of the treated liquid was evaporated to dryness under a reduced pressure, and the nicotinic acid content of the resulting crude crystals of nicotinamide was determined with N/10 caustic soda. The conversion of 3-cyanopyridine was 98.6%, the selectivity for nicotinamide was 97.9%, and that for nicotinic acid was 2.1%.

Example 2

From the mixed aqueous solutions containing nickel nitrate [$Ni(NO_3)_2 \cdot 6H_2O$] and ferric nitrate [$Fe(NO_3)_3 \cdot 9H_2O$] at various ratios, and aqueous ammonium carbonate solution, precipitates were formed at pH 7.5 – 8.5, similarly to above Example 1. The precipitates were recovered by filtration, washed with water, dried, and calcined for 3 hours in air at 400°C.

Each of the catalysts was used for the hydration of 3-cyanopyridine, in the manner identical with Example 1, with the results as indicated in Table 1 below.

Table 1

| Atomic Ratio of Catalyst Components Ni:Fe | Conversion of 3-Cyano-pyridine (%) | Selectivity for Nicotinamide (%) | Selectivity for Nicotinic Acid (%) |
|---|---|---|---|
| 10:1 | 88.0 | 98.5 | 1.5 |
| 5:1 | 98.7 | 97.7 | 2.3 |
| 3:1 | 98.2 | 97.6 | 2.4 |
| 1:1 | 97.3 | 96.9 | 3.1 |
| 0.5:1 | 96.1 | 94.8 | 5.2 |

Example 3

Each 0.5 g and 1 g of the catalyst prepared as in Example 1 were selected in 20-ml glass ampoules, each with 10 cc of a 10% (weight/volume) aqueous solution of 3-cyanopyridine. The two glass ampoules were placed in a thermostat with shaking apparatus, and the reaction was performed at 130°C. for 3 hours. Analyzing the reaction product by the similar method as described in Example 1, the conversion of 3-cyanopyridine in the former ampoule was 84.6%, and that in the second ampoule was 95.0%.

Example 4

One (1) g of 4-cyanopyridine and 10 cc of water were sealed in a 20-ml glass ampoule, together with 1 g of the catalyst used in Example 1. The reaction was effected under the same conditions as employed in Example 1. The conversion of 4-cyanopyridine was 97.4%, and the selectivity for isonicotinamide was 97.2%.

Control 1

In this experiment, nickel oxide alone was used as the catalyst.

From an aqueous nickel nitrate [$Ni(NO_3)_2 \cdot 6H_2O$] solution and an aqueous ammonium carbonate solution, a precipitate was formed similarly to Example 2. The precipitate was recovered by filtration, washed with water, dried for 9 hours at 110°C., and calcined for 3 hours at 400°C. in air, to form a catalyst. One (1) g of the catalyst was used in the hydration of 3-cyanopyridine performed in the identical manner with Example 1. As the result, the conversion of 3-cyanopyridine achieved was 69.2%, and the selectivity for nicotinamide was 98.6%.

Control 2

In the following experiment, iron oxide alone was used as the catalyst.

From an aqueous solution of ferric nitrate [$Fe(NO_3)_3 \cdot 9H_2O$] and an aqueous ammonium carbonate solution, a precipitate was formed similarly to Control 1. The precipitate was recovered by filtration, washed with water, dried, and calcined in air for 3 hours at 400°C. to provide a catalyst. One (1) g of this catalyst was used for the hydration of 3-cyanopyridine performd in the identical manner with Example 1. As the result, the conversion of 3-cyanopyridine achieved was 29.2%, and the selectivity for nicotinamide was 99.3%.

Example 5

The powders of nickel oxalate ($NiC_2O_4 \cdot 2H_2O$) and ferrous oxalate ($FeC_2O_4 \cdot 2H_2O$) were put in a mortar at the quantitative ratio as would make the atomic ratio of Ni to Fe 5:1, and thoroughly ground and mixed. The mixture was heated in air for 10 hours at 300°C. to form a catalyst. Using 2 g of the so-formed catalyst and 10 cc of a 10% (weight/volume) aqueous solution of 3-cyanopyridine, the hydration reaction similar to that of Example 1 was performed for 4 hours at 120°C. As the result, the conversion was 78.9%, and the selectivity for nicotinamide was 99.1%.

Example 6

An intimate mixture of nickel-iron hydroxides formed by the co-precipitation method using nickel sulfate, ferric sulfate and caustic soda, in the manner similar to Example 1, was calcined in air for 6 hours at 350°C. to provide a catalyst. 0.5 Gram of the catalyst was sealed into a 20-ml glass ampoule together with 2 g of 3-cyanopyridine and 8 g of water, and the ampoule was shaken for 2.5 hours at 150°C.

As the result of the hydration reaction, the conversion was 85.8%, and the selectivity for nicotinamide was 98.7%.

Example 7

An intimate mixture of nickel-iron hydroxides formed by the co-precipitation method similar to that of Example 1, using nickel sulfate, ferric sulfate, and sodium carbonate, was calcined in air at 350°C. for 2 hours to provide a catalyst.

Four (4) g of this catalyst was added to 50 cc of a 5% (weight/volume) aqueous solution of 3-cyanopyridine, and together stirred for 2 hours under reflux.

As the result, the conversion of 3-cyanopyridine was 73.4%, and the selectivity for nicotinamide was 99.1%.

Example 8

1164 Grams of nickel nitrate and 324 g of ferric nitrate were dissolved in 4 liters of water. Separately, 876 g of ammonium carbonate was dissolved in 3 liters of water, and the two solutions were dropped into 1.2 liters of water under stirring, at a pH maintained at 8.5, consuming 1.5 hours. Thereafter the system was further stirred for an hour, and the formed precipitate was recovered by filtration, washed with water, dried in hot air current of 110°C. for 6 hours, and then calcined at 500°C. for 4 hours. The resulting combined oxide was molded into tablets with a tabletting machine, which were granulated and sieved to provide the catalyst of the average diameter 0.5 – 1.0 mm. Seventy-five (75) g of this granular catalyst was packed in a stainless steel tubular reactor of 21.6 mm in inner diameter and 80 ml in capacity. While maintaining the temperature and pressure of the system at 130°C. and 6 kg/cm$^2$, a 20% (weight/weight) aqueous 3-cyanopyridine solution preheated to 85°C. was fed into the tube from the bottom of the catalyst bed, at the flow rate of 1.6 liters/kg.cat./hr. (3.3 mols/kg.cat./hr.). Analyzing the reaction liquid obtained at the exit provided on an upper part of the packed column in the manner similar to Example 1, the conversion after 10 hours' reaction was 97.4%, and the selectivity for nicotinamide was 98.5%. The conversion after 70 hours' reaction was 97.2%, and the selectivity for nicotinamide was 98.5%.

Example 9

A part of the combined hydroxides prepared in Example 8 was calcined at 400°C. for 4 hours, and subsequently processed similarly to Example 8 to provide a catalyst of the average grain diameter 0.5 – 1.0 mm. This catalyst was used in the hydration under the identical reaction conditions with those of Example 8. The conversion after 10 hours' reaction was 99.4%, the selectivity for nicotinamide was 98.2%, and that for nicotinic acid was 1.8%.

Example 10

A catalyst was formed similarly to Example 9, except that the combined hydroxides were calcined at 600°C. for 4 hours. The reaction tube as employed in Example 8 was packed with this catalyst, and while it was maintained at a temperature and pressure of 140°C. and 7 kg/cm$^2$, a 20% (weight/weight) aqueous 3-cyanopyridine solution was fed thereinto at a flow rate of 0.7 liter/kg.cat./hr. (1.4 mols/kg.cat./hr.). Analyzing the reaction liquid by the similar method as employed in Example 1, the conversion after 10 hours' reaction was 93.1%, the selectivity for nicotinamide was 98.5%, and that for nicotinic acid was 1.5%.

Example 11

An intimate mixture of nickel-iron hydroxides prepared similarly to Example 8 from nickel sulfate, ferric sulfate, and sodium carbonate, was calcined at 500°C. for 2 hours, and thereafter treated similarly to Example 8, to form the granular catalyst of the average diameter ranging from 1.7 to 3.4 mm. This catalyst was filled in the identical reaction apparatus with that employed in Example 8. While maintaining the system at the reaction temperature and pressure of 130°C. and 6 kg/cm$^2$, a 5% (weight/weight) aqueous 3-cyanopyridine solution was fed thereinto at a flow rate of 2.0 liters/kg.cat./hr. (1.0 mol/kg.cat./hr.). Analyzing the reaction liquid in the manner similar to Example 1, it was confirmed that the conversion after 10 hours' reaction was 88.5%, the selectivity for nicotinamide was 98.1%, and that for nicotinic acid was 1.9%.

We claim:

1. A method for the production of nicotinamide or isonicotinamide by catalytically hydrating 3-or 4-cyanopyridine which is characterized in that the hydration reaction is carried out in the presence of a nickel oxide/iron oxide combined catalyst.

2. The method of claim 1, in which the atomic ratio of Ni to Fe in the combined catalyst ranges from 100:1 to 1:100.

3. The method of claim 2, in which the atomic ratio of Ni to Fe ranges from 10:1 to 1:10.

4. The method of claim 1, in which the combined catalyst is that obtained by calcining an intimate mixture of the hydroxides of nickel and iron, or that of water-soluble salts of nickel and iron, at a temperature within the range of 100° to 1000°C.

5. The method of claim 4, in which the calcining temperature ranges from 200° to 800°C.

6. The method of claim 5, in which the calcining temperature ranges from 300° to 600°C.

7. The method of claim 1, in which the hydration reaction is performed in the presence of 1 to 100 times the stoichiometric amount of water, at liquid phase, at the reaction temperature ranging from room temperature to 300°C.

8. The method of claim 7, in which the amount of the water is 5 to 50 times the stoichiometric amount.

9. The method of claim 7, in which the reaction temperature ranges from 50° to 200°C.

* * * * *

UNITED STATES PATENT OFFICE
CERTIFICATE OF CORRECTION

Patent No. 3,957,804     Dated May 18, 1976

Inventor(s) RYOJI ISHIOKA, ET AL.

It is certified that error appears in the above-identified patent and that said Letters Patent are hereby corrected as shown below:

Column 1, line 46, "hour" to read -- hours --;

Column 4, line 10, "[Nl(NO$_3$)$_2 \cdot$6H$_2$O]" to read -- [Ni(NO$_3$)$_2 \cdot$6H$_2$O] --;

Column 6, line 16, delete "were dissolved", second instance.

Signed and Sealed this

Third Day of August 1976

[SEAL]

Attest:

RUTH C. MASON
Attesting Officer

C. MARSHALL DANN
Commissioner of Patents and Trademarks